United States Patent
Hachisuka et al.

(10) Patent No.: US 10,864,922 B2
(45) Date of Patent: Dec. 15, 2020

(54) WAKEFULNESS MAINTENANCE APPARATUS

(71) Applicant: DENSO CORPORATION, Kariya (JP)

(72) Inventors: Satori Hachisuka, Kariya (JP); Masaru Kakizaki, Kariya (JP); Eiichi Okuno, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 16/584,019

(22) Filed: Sep. 26, 2019

(65) Prior Publication Data

US 2020/0017125 A1 Jan. 16, 2020

Related U.S. Application Data

(63) Continuation of application No. PCT/JP2018/011389, filed on Mar. 22, 2018.

(30) Foreign Application Priority Data

Mar. 27, 2017 (JP) .................................. 2017-061332

(51) Int. Cl.
*B60W 50/16* (2020.01)
*B60W 40/08* (2012.01)
(Continued)

(52) U.S. Cl.
CPC ............ *B60W 50/16* (2013.01); *B60W 40/08* (2013.01); *G06K 9/00845* (2013.01);
(Continued)

(58) Field of Classification Search
CPC ........................................................ A61B 5/04
See application file for complete search history.

(56) References Cited

U.S. PATENT DOCUMENTS

6,070,098 A * 5/2000 Moore-Ede .......... A61B 5/1103
600/300
2009/0231146 A1 9/2009 Fujita
(Continued)

FOREIGN PATENT DOCUMENTS

JP H11-025399 A 1/1999
JP 2007-021019 A 2/2007
(Continued)

*Primary Examiner* — Nabil H Syed
*Assistant Examiner* — Cal J Eustaquio
(74) *Attorney, Agent, or Firm* — Maschoff Brennan

(57) ABSTRACT

A wakefulness maintenance apparatus includes a presentation recording unit and a presentation execution unit. The presentation recording unit records in-vehicle presentation contents each including a corresponding one of scenes, an auditory stimulus action associated with the scene, and at least one stimulus action selected from a group of a visual stimulus action, a tactile stimulus action, and an olfactory stimulus action which are associated with the scene. The presentation execution unit executes, based on the in-vehicle presentation contents recorded in the presentation recording unit, an in-vehicle presentation including provision of: the auditory stimulus action associated with the scene, and the at least one stimulus action selected from the group of the visual stimulus action, tactile stimulus action, and olfactory stimulus action which are associated with the scene.

8 Claims, 8 Drawing Sheets

(51) Int. Cl.
*G06K 9/00* (2006.01)
*B60W 50/14* (2020.01)
(52) U.S. Cl.
CPC ............... *B60W 2040/0827* (2013.01); *B60W 2050/143* (2013.01); *B60W 2050/146* (2013.01)

(56) References Cited

U.S. PATENT DOCUMENTS

2014/0300478 A1   10/2014   Kume et al.
2017/0080856 A1   3/2017    Enomoto et al.

FOREIGN PATENT DOCUMENTS

| | | |
|---|---|---|
| JP | 2009-031840 A | 2/2009 |
| JP | 2014-071628 A | 4/2014 |
| JP | 2016-088497 A | 5/2016 |
| JP | 2016-168933 A | 9/2016 |
| JP | 2016-192127 A | 11/2016 |

\* cited by examiner

FIG.3

SEA

| SCENE | IMAGE | BASIC INFORMATION | VISUAL STIMULUS INFORMATION | AUDITORY STIMULUS INFORMATION | TACTILE STIMULUS INFORMATION | OLFACTORY STIMULUS INFORMATION | ... | AWAKENING EFFECT |
|---|---|---|---|---|---|---|---|---|
| HAWAII BEACH | | · DATE AND TIME<br>· LOCATION<br>· REPRODUCTION TIME | · BLUE, WHITE<br>· CHANGE PATTERN A1 | · WAVE SOUND B1<br>· WILD BIRD<br>· HAWAIIAN BGM | · LIGHT WIND<br>· SUNLIGHT (DAYTIME) | · SUNSCREEN (MOLECULE C1)<br>· COCONUT (MOLECULE C2) | ... | 1 |
| ... | ... | ... | ... | ... | ... | ... | ... | ... |
| OKINAWA DUSK | | · DATE AND TIME<br>· LOCATION<br>· REPRODUCTION TIME | · RED, ORANGE, BLUE<br>· CHANGE PATTERN A2 | · WAVE SOUND B2<br>· EVENING CICADA<br>· RYUKYUAN BGM | · LIGHT WIND | — | ... | 1 |
| JAPAN SEA FISHING BOAT | | · DATE AND TIME<br>· LOCATION<br>· REPRODUCTION TIME | · MAZARINE, WHITE<br>· CHANGE PATTERN A3 | · WAVE SOUND B3<br>· GULL<br>· SHIP ENGINE SOUND | · STRONG WIND<br>· SPRAY | · SEA BREEZE (MOLECULE C3)<br>· OCEAN (MOLECULE C4) | ... | 3 |
| ... | ... | ... | ... | ... | ... | ... | ... | ... |
| ... | ... | ... | ... | ... | ... | ... | ... | ... |
| — | — | — | — | — | — | — | ... | — |

FIG.4

| SCENE | IMAGE | FIREWORK | | | |
|---|---|---|---|---|---|
| | | BASIC INFORMATION | VISUAL STIMULUS INFORMATION | ⋮ | AWAKENING EFFECT |
| ATAMI FIREWORKS EVENT | 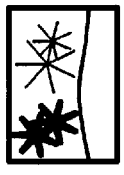 | · DATE AND TIME<br>· LOCATION<br>· REPRODUCTION TIME | · RED, ORANGE, GREEN<br>· CHANGE PATTERN A4 | ⋮ | 2 |
| ⋯ | ⋯ | ⋯ | ⋯ | ⋯ | ⋯ |
| VERANDA IN-HAND FIREWORK | 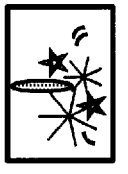 | · DATE AND TIME<br>· LOCATION<br>· REPRODUCTION TIME | · RED, ORANGE, BLUE<br>· CHANGE PATTERN A5 | ⋮ | 2 |
| ATAMI FIREWORKS EVENT |  | · DATE AND TIME<br>· LOCATION<br>· REPRODUCTION TIME | · RED, ORANGE, GREEN<br>· CHANGE PATTERN A6 | ⋮ | 2 |
| ⋯ | ⋯ | ⋯ | ⋯ | ⋯ | ⋯ |
| ⋯ | ⋯ | ⋯ | ⋯ | ⋯ | ⋯ |
| AMUSEMENT PARK | 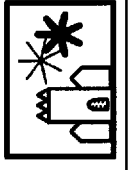 | · DATE AND TIME<br>· LOCATION<br>· REPRODUCTION TIME | · WHITE, YELLOW, RED<br>· CHANGE PATTERN A6 | ⋮ | 4 |
| ⋮ | ⋮ | ⋮ | ⋮ | ⋮ | ⋮ |

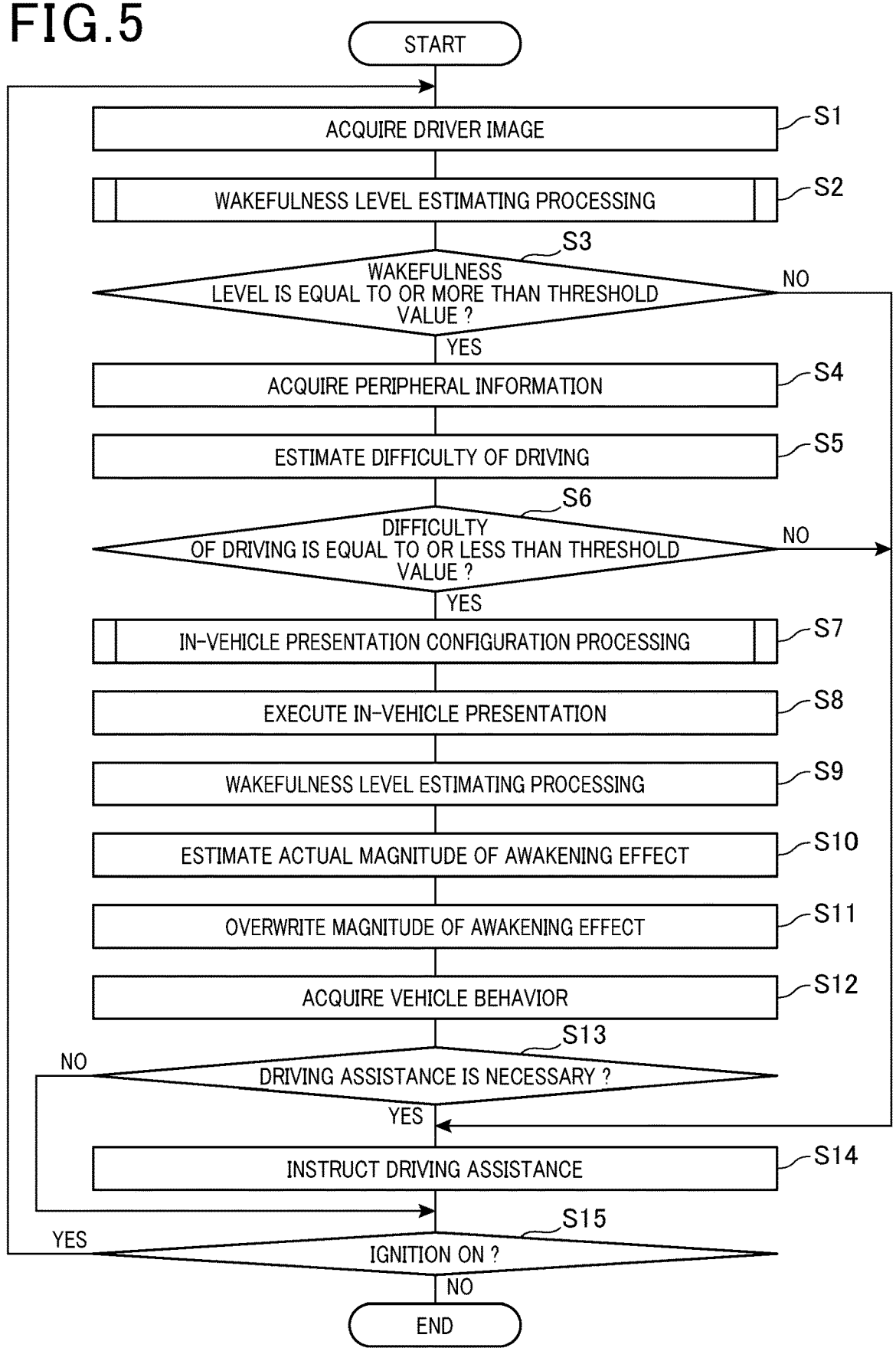

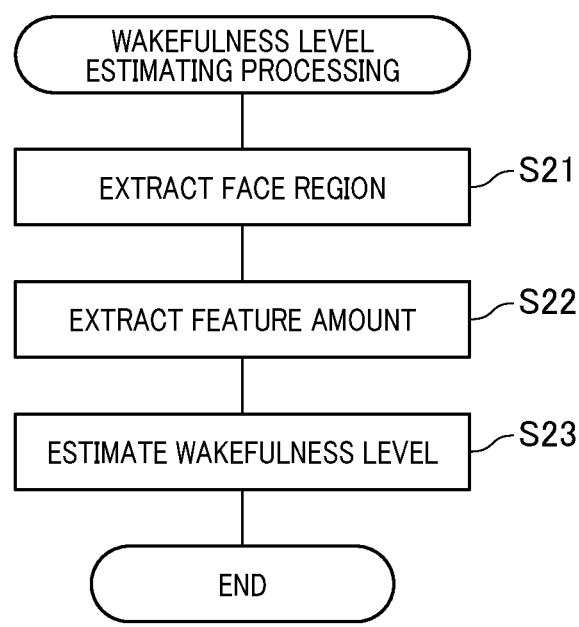

WAKEFULNESS MAINTENANCE APPARATUS

CROSS-REFERENCE TO RELATED APPLICATION

The present application is a continuation application of International Application No. PCT/JP2018/011389, filed on Mar. 22, 2018, which claims priority to Japanese Patent Application No. 2017-61332, filed on Mar. 27, 2017. The contents of these applications are incorporated herein by reference in their entirety.

BACKGROUND

Technical Field

The present disclosure relates to a wakefulness maintenance apparatus.

Background Art

Wakefulness of a driver is maintained by using a sensory stimulation such as sound.

SUMMARY

In one aspect of the present disclosure, there is provided a wakefulness maintenance apparatus including a presentation recording unit that records in-vehicle presentation contents each including: a corresponding one of scenes, an auditory stimulus action associated with the scene, and at least one stimulus action selected from a group of a visual stimulus action, a tactile stimulus action, and an olfactory stimulus action which are associated with the scene; and a presentation execution unit that executes, based on the in-vehicle presentation contents recorded in the presentation recording unit, an in-vehicle presentation including provision of: the auditory stimulus action associated with the scene, and the at least one stimulus action selected from the group of the visual stimulus action, tactile stimulus action, and olfactory stimulus action which are associated with the scene.

BRIEF DESCRIPTION OF THE DRAWINGS

FIG. 3 is an explanatory diagram showing an example of in-vehicle presentation contents recorded in a recording unit.

FIG. 4 is an explanatory diagram showing an example of in-vehicle presentation contents recorded in the recording unit.

FIG. 5 is a flowchart showing whole processing executed by the wakefulness maintenance apparatus.

FIG. 6 is a flowchart showing wakefulness level estimating processing executed by the wakefulness maintenance apparatus.

DETAILED DESCRIPTION OF THE PREFERRED EMBODIMENTS

PTL 1 discloses a technology of adjusting a driving environment by using a fluctuation sound, an aroma, and a color of decoration in a vehicle compartment and of matching a mental condition of a driver to an operating condition of a driving assistance apparatus.

[PTL 1] JP 2007-21019 A

It may be considered to maintain wakefulness of a driver by using a sensory stimulus such as sound. However, as a result of detailed study of the inventor, there is found a problem that since the driver is gradually accustomed to the sensory stimulus, it is difficult to maintain wakefulness of the driver by the conventional sensory stimulus. In one aspect of the present disclosure, it is preferable to provide a wakefulness maintenance apparatus capable of maintaining wakefulness of a driver.

The wakefulness maintenance apparatus as one aspect of the present disclosure can execute the in-vehicle presentation. The in-vehicle presentation includes application of an auditory stimulus action associated with the scene and at least one stimulus action selected from a group of a visual stimulus action, a tactile stimulus action, and an olfactory stimulus action which are associated with the scene, and thus a driver can be made to associate a scene with it. Therefore, cognitive activity of the driver increases and memory is recalled, and thereby the feeling is changed. That is, a higher-order function of a brain of the driver can be activated. As a result, the driver is less likely to become accustomed to the in-vehicle presentation and it is possible to maintain wakefulness of the driver.

Exemplary embodiments of the present disclosure will be described with reference to drawings.

First Embodiment

1. Configuration of Wakefulness Maintenance Apparatus 1

Figure 1:
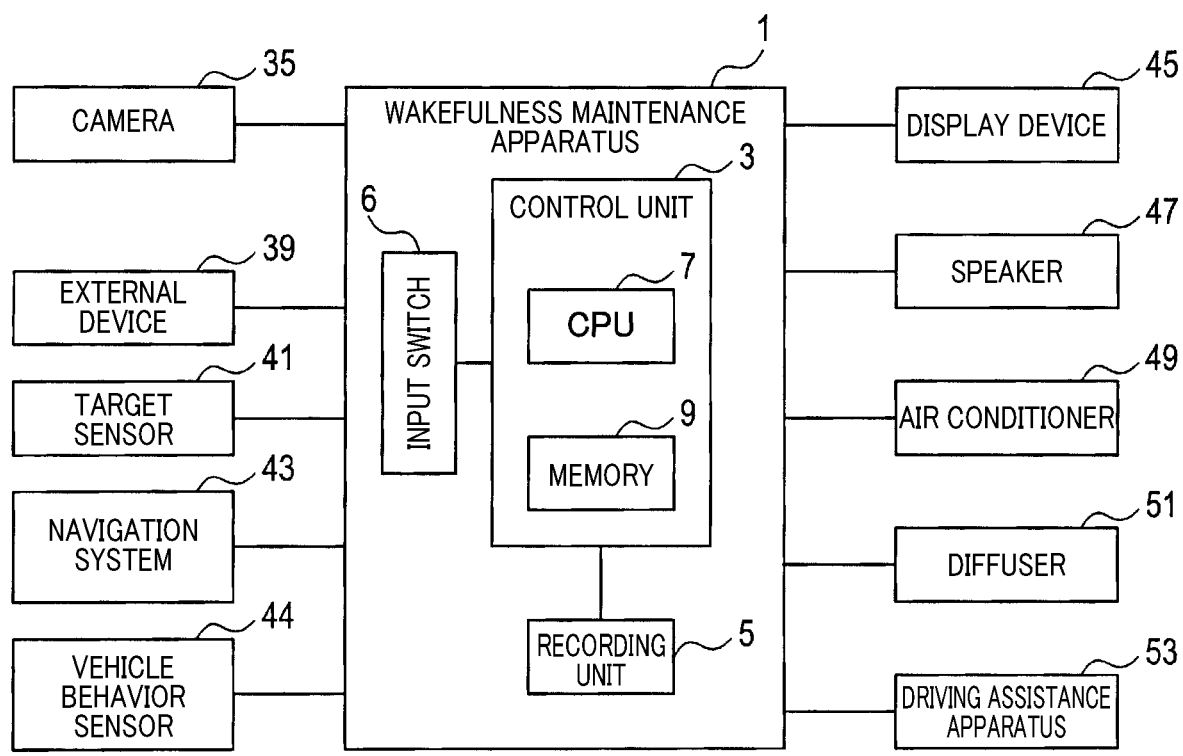
FIG. 1 is a block diagram showing a configuration of a wakefulness maintenance apparatus.

The configuration of a wakefulness maintenance apparatus 1 will be described based on FIG. 1 to FIG. 4. The wakefulness maintenance apparatus 1 is an on-vehicle apparatus mounted on a vehicle. The vehicle mounting the wakefulness maintenance apparatus 1 will be referred to as an own vehicle in the following. As shown in FIG. 1, the wakefulness maintenance apparatus 1 includes a control unit 3, a recording unit 5, and an input switch 6. Note that the recording unit 5 corresponds to a presentation recording unit and a recording apparatus.

The control unit 3 is configured mainly by a well-known microcomputer having a CPU 7 and semiconductor memories (hereinafter, referred to as a memory 9) such as a RAM, a ROM, and a flash memory. Various functions of the control unit 3 are implemented by the CPU 7 executing one or more programs stored in a non-transitory tangible recording medium. In this example, the memory 9 corresponds to the non-transitory tangible recording medium storing the program. In addition, when the program is executed, a method corresponding to the program is executed. Note that, the number of microcomputers constituting the control unit 3 may be one or more.

Figure 2:
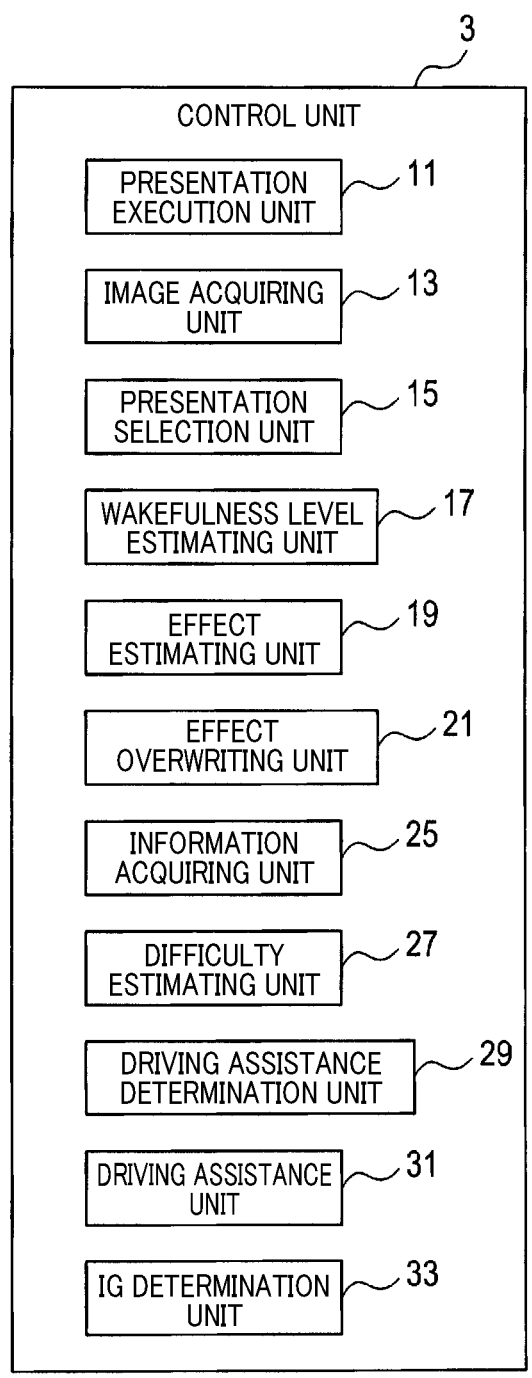
FIG. 2 is a block diagram showing a functional configuration of a control unit.

The control unit 3, as a configuration of functions realized by the CPU 7 executing the program, as shown in FIG. 2, includes a presentation execution unit 11, an image acquiring unit 13, a presentation selection unit 15, a wakefulness level estimating unit 17, an effect estimating unit 19, an effect overwriting unit 21, an information acquiring unit 25, a difficulty estimating unit 27, a driving assistance determination unit 29, a driving assistance unit 31, and an IG determination unit 33.

The method of realizing these elements constituting the control unit 3 is not limited to software, but a part or all of these elements may be realized by using one or more hardware components. For example, when the above-described functions are realized by an electronic circuit that is hardware, the electronic circuit may be realized by a digital circuit including many logic circuits, or an analog circuit, or a combination of these circuits.

The recording unit 5 records in-vehicle presentation contents. The in-vehicle presentation contents specify contents of in-vehicle presentation to be described below. Each of the in-vehicle presentation contents, as shown in FIG. 3 and FIG. 4, is information associating a scene, an image, basic information, visual stimulus information, auditory stimulus information, tactile stimulus information, and olfactory stimulus information with each other. The recording unit 5 records a plurality of in-vehicle presentation contents. In FIG. 3 and FIG. 4, one row represents one in-vehicle presentation content.

The scene means a location, a clock time, season, weather, an object in the periphery, and situation defined by human action or the like. Examples of the scene include "Hawaii beach", "dusk in Okinawa", "fishing boat in Japan Sea", "fireworks in Atami", "hand-held firework on veranda", and "amusement park".

The image is an image showing the associated scene. The basic information is information including a date and time of the scene, a location of the scene, a reproduction time of the in-vehicle presentation, and the like.

The visual stimulus information specifies a visual stimulus action provided in the in-vehicle presentation. The visual stimulus action is comprised of one or more light stimuli applied to a driver of the own vehicle. The visual stimulus information about the visual stimulus action, which specifies the visual stimulus action, includes, for example, a color of each light stimulus, a strength of each light stimulus, a pattern of time-series changes of the colors and/or strengths of the light stimuli, a start timing of application of the visual stimulus action, and the like. In addition, for example, when a plurality of devices that emit light are installed in the vehicle, a location or the like of each apparatus that emits light is also a factor for specifying the visual stimulus action. The visual stimulus action specified by the visual stimulus information is a visual stimulus action generated in the associated scene.

The auditory stimulus information specifies an auditory stimulus action provided in the in-vehicle presentation. The auditory stimulus action is comprised of one or more sound stimuli applied to a driver of the own vehicle. The auditory stimulus information about the auditory stimulus action, which specifies the auditory stimulus action, includes, for example, a loudness of each sound stimulus, a frequency of each sound stimulus, a pattern of time-series changes of the loudness and/or frequencies of the sound stimuli, a start timing of application of the auditory stimulus action, and the like. In addition, for example, when a plurality of devices that generate sound are installed in the vehicle, a location or the like of each apparatus that generates sound is also a factor for specifying the auditory stimulus action. Examples of the auditory stimulus action include one or more wave sounds, one or more chirp sounds of a wild bird or an insect, music, one or more engine sounds, and the like. The auditory stimulus action specified by the auditory stimulus information is an auditory stimulus action generated in the associated scene.

The tactile stimulus information specifies a tactile stimulus action provided in the in-vehicle presentation. The tactile stimulus action is comprised of one or more wind stimuli applied to a driver of the own vehicle. The tactile stimulus information about the tactile stimulus action, which specifies the tactile stimulus action, includes, for example, a strength of each wind stimulus, a direction of each wind stimulus, a pattern of time-series changes of the strengths and/or directions of the wind stimuli, a start timing of application of the tactile stimulus action, and the like. In addition, for example, when a plurality of devices that generate wind are installed in the vehicle, a location or the like of each apparatus that generates wind is also a factor for specifying the tactile stimulus action. Examples of the tactile stimulus action include one or more light winds, one or more strong winds, and the like. In addition, the tactile stimulus action may be a stimulus by vibration, pressure, temperature, or the like. The tactile stimulus action specified by the tactile stimulus information is a tactile stimulus action generated in the associated scene.

The olfactory stimulus information specifies an olfactory stimulus action provided in the in-vehicle presentation. The olfactory stimulus action is comprised of one or more aromatic stimuli applied to a driver of the own vehicle. The olfactory stimulus information about the olfactory stimulus action, which specifies the olfactory stimulus action, includes, for example, a type of each aromatic stimulus, a strength of each aromatic stimulus, a pattern of time-series changes of the types and/or strengths of the aromatic stimuli, a start timing of application of the olfactory stimulus action, and the like. In addition, for example, when a plurality of devices that generate aroma are installed in the vehicle, a location or the like of each apparatus that generates aroma is also a factor for specifying the olfactory stimulus action. Examples of the olfactory stimulus action include one or more sunscreen-flavored stimuli, one or more coconut-flavored stimuli, one or more sea-breeze-flavored stimuli, one or more ocean-flavored stimuli, and the like. The olfactory stimulus action specified by the olfactory stimulus information is an olfactory stimulus action generated in the associated scene.

Each of the in-vehicle presentation contents includes an order of starting provision (hereinafter, referred to as a stimulus order) of a visual stimulus action, an auditory stimulus action, a tactile stimulus action, and an olfactory stimulus action. Examples of the stimulus order include an order of starting provision of the visual stimulus action and auditory stimulus action at first and then starting provision of the tactile stimulus action and olfactory stimulus action.

In addition, for example, the stimulus order may be an order based on a strength of connection between each sensory stimulus and a scene. The strength of connection between each sensory stimulus and a scene, for example, uses as an index a probability or the like with which a scene can be specified by a single stimulus.

The recording unit 5 records a corresponding magnitude of awakening effect in association with an in-vehicle presentation content. The corresponding magnitude of awakening effect means a corresponding magnitude of effect of awakening a driver by executing the in-vehicle presentation. The corresponding magnitude of awakening effect is represented by the numerical value. The larger the numerical value is, the higher the awakening effect is.

The recording unit 5 can record an image. The driver can record an image into the recording unit 5. Examples of the image recorded in the recording unit 5 include a camera image photographed by the driver. The recording unit 5 can record an image tag in association with an image. The image tag includes a date and time when the image was recorded, a location where the image was recorded, a name of a person who created the image, and the like.

In addition, the image tag includes information (hereinafter, referred to as driver preference information) tagged based on preference by the driver after photographing. The driver preference information indicates a corresponding magnitude of the preference level of the driver for an image. The driver preference information, for example, includes a type of a storage folder for classifying an image, an index of evaluation on an image itself, and the like. The image stored in a specific storage folder has a higher preference level of a driver than an image stored in another storage folder. In addition, the higher the index of evaluation on an image itself is, the higher the preference level of a driver is.

The input switch 6 is provided in a vehicle compartment of the own vehicle and receives an input operation of an occupant. The occupant operating the input switch 6 may be a driver or may be an occupant other than the driver. The input switch 6 corresponds to an input unit.

As shown in FIG. 1, the own vehicle includes, in addition to the wakefulness maintenance apparatus 1, a camera 35, an external apparatus 39, a target sensor 41, a navigation system 43, a vehicle behavior sensor 44, a display apparatus 45, a speaker 47, an air conditioner 49, a diffuser 51, and a driving assistance apparatus 53.

The camera 35 photographs a range including a driver's face to generate an image (hereinafter, referred to as a face image). The camera 35 is attached to any of a steering column, a dashboard, a ceiling of a vehicle compartment, and the like of the own vehicle.

The external apparatus 39 is a apparatus capable of recording an image. The driver can record an image into the external apparatus 39. Examples of the image recorded in the external apparatus 39 include a camera image photographed by the driver. Examples of the external apparatus 39 include a mobile terminal. Examples of the mobile terminal include a smartphone. The external apparatus 39 can record an image tag in association with an image. The image tag includes a date and time when the image was recorded, a location where the image was recorded, a name of a person who created the image, the driver preference information, and the like. Note that the external apparatus 39 corresponds to a recording apparatus.

The target sensor 41 detects a target existing around the own vehicle. Examples of the target include another vehicle, a pedestrian, and a feature. Examples of the target sensor 41 include an on-vehicle camera and a laser radar.

The navigation system 43 can acquire a location of the own vehicle, an environment of a road, traffic congestion information, and the like.

The vehicle behavior sensor 44 detects the behavior of the own vehicle. Examples of the behavior of the own vehicle include a speed, an acceleration, a yaw rate, an angle formed between a traveling direction of the own vehicle and a white line, and a relative position of the own vehicle with respect to a lane.

The display apparatus 45 is provided in a vehicle compartment of the own vehicle. The display apparatus 45 can provide a visual stimulus action to a driver of the own vehicle by irradiating light. The display apparatus 45 can change a color of light, a strength of light, an irradiation direction of light, presence or absence of blinking of light, an irradiation range of light, and the like.

The speaker 47 is provided in a vehicle compartment of the own vehicle. The speaker 47 can provide an auditory stimulus action to a driver of the own vehicle by outputting sound. The speaker 47 can change a loudness of sound, a frequency of sound, and the like.

The air conditioner 49 is provided in a vehicle compartment of the own vehicle. The air conditioner 49 can provide a tactile stimulus action to a driver of the own vehicle by jetting wind. The air conditioner 49 can change a strength of wind, a direction of wind, a temperature of wind, a humidity of wind, and the like.

The diffuser 51 is provided in a vehicle compartment of the own vehicle. The diffuser 51 can provide an olfactory stimulus action to a driver of the own vehicle by emitting aroma. The diffuser 51 includes many fragrances. The diffuser 51 can select one or more fragrances from among the many fragrances and emit aromas of the selected fragrances. That is, the diffuser 51 can change a type of aroma. In addition, the diffuser 51 can change also a strength of aroma.

The driving assistance apparatus 53 can perform driving assistance. Examples of the driving assistance include processing to warn the driver with sound, vibration, video, or the like when another vehicle approaching the own vehicle exists. In addition, examples of the driving assistance, when meandering, inappropriate speed fluctuation, or the like has occurred in the own vehicle, include processing to perform automatic steering and automatic speed adjustment in order to suppress them.

2. Processing Executed by the Wakefulness Maintenance Apparatus 1

The processing executed by the wakefulness maintenance apparatus 1 will be described based on FIG. 5 to FIG. 9. This processing is started, for example, when a predetermined operation is performed on the input switch 6.

In Step 1 of FIG. 5, the wakefulness level estimating unit 17 acquires a face image by using the camera 35.

In Step 2, the wakefulness level estimating unit 17 estimates a wakefulness level of a driver by using the face image acquired in the Step 1. This processing will be described based on FIG. 6. In Step 21 of FIG. 6, the wakefulness level estimating unit 17 extracts a region (hereinafter, referred to as a face region) occupied by the face of the driver in the face image.

In Step 22, the wakefulness level estimating unit 17 extracts a feature amount of the face in the face region by a method of image analysis. The feature amount of the face is, for example, movement of an eyebrow, movement of an eyelid, movement of a mouth, or the like.

In Step 23, the wakefulness level estimating unit 17 estimates a wakefulness level of the driver by collating the feature amount of the face extracted in the Step 22 with a database preliminarily recorded in the recording unit 5. The wakefulness level is represented by a numerical value. The larger the numerical value of the wakefulness level is, the higher a degree of wakefulness of the driver is. The wakefulness level to be estimated here corresponds to a wakefulness level before execution of the in-vehicle presentation.

Returning to FIG. 5, in Step 3, the wakefulness level estimating unit 17 determines whether the wakefulness level estimated in the Step 2 is equal to or more than a preset threshold value. The process proceeds to Step 4 when the wakefulness level is equal to or more than the threshold value, and proceeds to Step 14 when the wakefulness level is less than the threshold value.

In Step 4, the information acquiring unit 25 acquires peripheral information by using the target sensor 41 and the navigation system 43. Examples of the peripheral information include road environment around the own vehicle, traffic congestion state around the own vehicle, information on another vehicle and a pedestrian existing around the own vehicle, and the like.

In Step 5, the difficulty estimating unit 27 estimates difficulty of driving by collating the peripheral information acquired in the Step 4 with a database preliminarily recorded in the recording unit 5. The difficulty of driving is represented by a numerical value. As the numerical value of difficulty is larger, driving is difficult.

In Step 6, the difficulty estimating unit 27 determines whether the difficulty of driving estimated in the Step 5 is equal to or less than a preset threshold value. The process proceeds to Step 7 when the difficulty of driving is equal to or less than the threshold value, and proceeds to Step 14 when the difficulty of driving exceeds the threshold value.

In Step 7, the presentation selection unit 15 and the image acquiring unit 13 execute the in-vehicle presentation configuration processing. This processing will be described based on FIG. 7.

Figure 7:
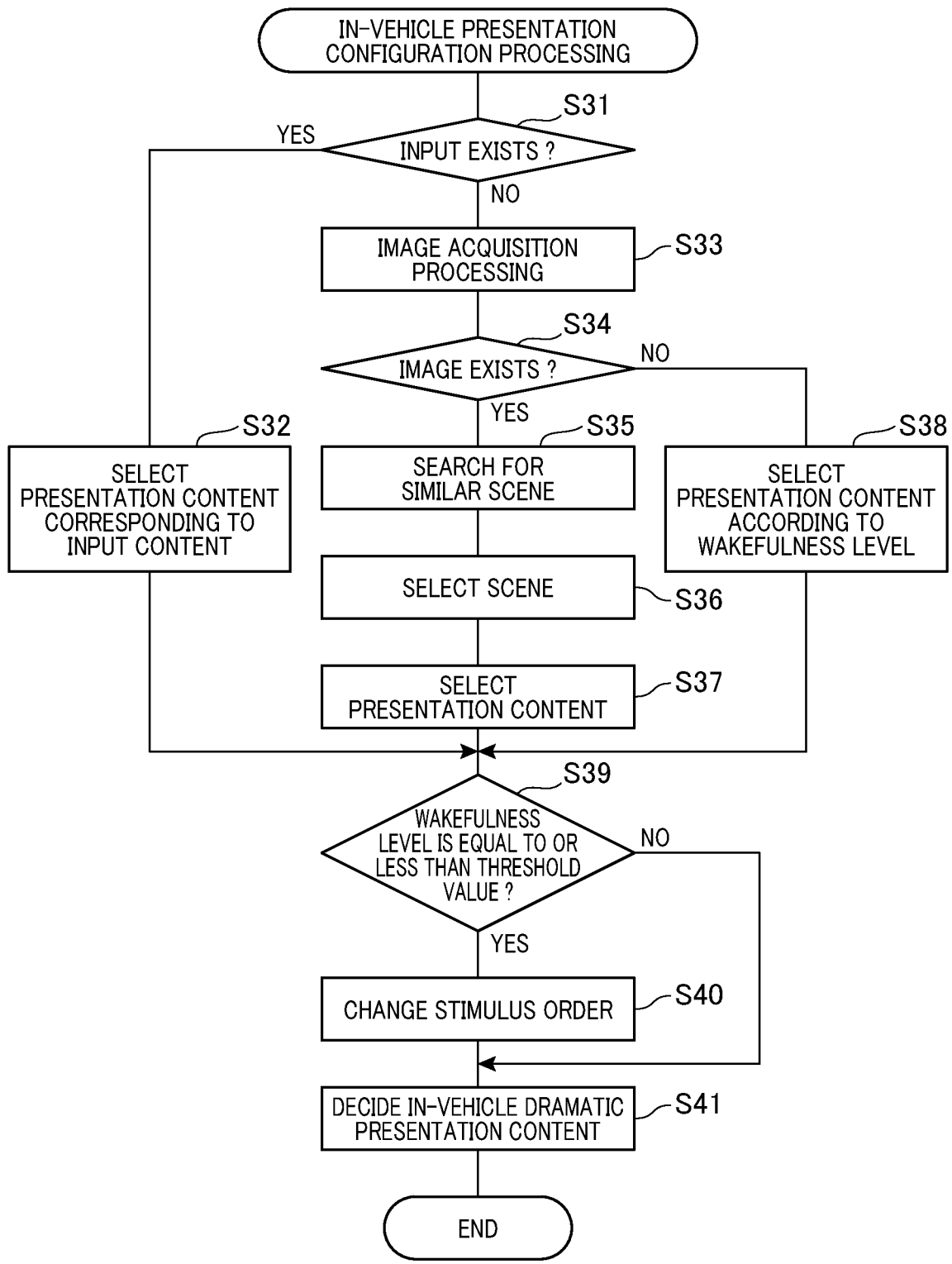
FIG. 7 is a flowchart showing in-vehicle presentation configuration processing executed by the wakefulness maintenance apparatus.

In Step 31 of FIG. 7, the presentation selection unit 15 determines whether an input operation to designate an in-vehicle presentation content (hereinafter, referred to as a designation operation) has been performed on the input switch 6. The process proceeds to Step 32 when the designation operation was performed, and proceeds to Step 33 when the designation operation was not performed.

In Step 32, the presentation selection unit 15 selects the in-vehicle presentation content designated by the designation operation from among the in-vehicle presentation contents recorded in the recording unit 5. Note that, the in-vehicle presentation content designated by the designation operation correspond to the input content.

In Step 33, the image acquiring unit 13 performs processing to acquire an image from the external apparatus 39 or the recording unit 5. At this time, the image acquiring unit 13 first performs processing to acquire an image in the external apparatus 39. When an image to be acquired does not exist in the external apparatus 39, the image acquiring unit 13 performs processing to acquire an image in the recording unit 5. When a plurality of images are recorded in the external apparatus 39 or the recording unit 5, the image acquiring unit 13 preferentially acquires an image having a higher driver preference level represented by the driver preference information.

For images for which the driver preference information does not exist, the image acquiring unit 13 preferentially acquires an image having a newer date and time when the image was recorded. When a plurality of images having the same driver preference level exist, the image acquiring unit 13 preferentially acquires an image having a newer date and time when the image was recorded among the images.

In Step 34, the image acquiring unit 13 determines whether an image was able to be acquired in the Step 33. The process proceeds to Step 35 when an image was able to be acquired, and proceeds to Step 38 when an image was not able to be acquired.

In Step 35, the presentation selection unit 15 searches the recording unit 5 for a scene having a high degree of similarity with the image acquired in the Step 33.

For example, the degree of similarity can be determined by comparing the result of automatic image analysis of the image acquired in the Step 33 with the scene recorded in the recording unit 5. In addition, it can be determined by comparing an image tag attached to the image acquired in the Step 33 with the scene or basic information recorded in the recording unit 5.

Figure 8:
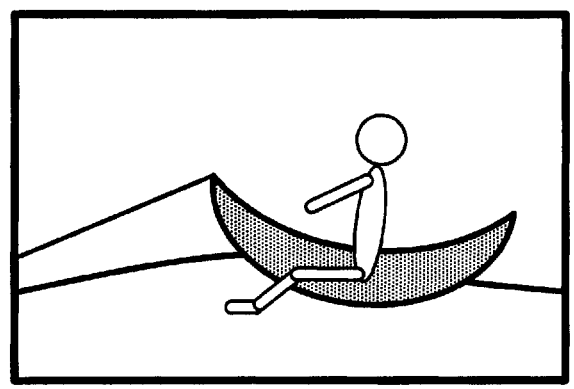
FIG. 8 is an explanatory diagram showing an example of an image acquired from an external apparatus or the recording unit.

For example, it is assumed that an image shown in FIG. 8 was acquired in the Step 33. The presentation selection unit 15 performed automatic image analysis on this image and as a result acquired words of "sea" and "banana boat". In this case, the presentation selection unit 15 can find out a scene of "Hawaii beach" as a scene having the highest degree of similarity and find out a scene of "ship deck" as a scene having the next highest degree of similarity in the scenes recorded in the recording unit 5.

Figure 9:
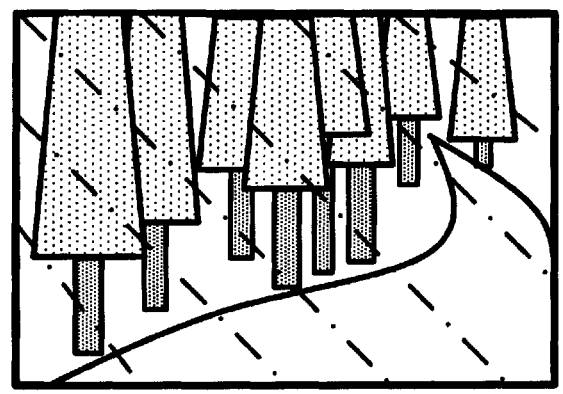
FIG. 9 is an explanatory diagram showing an example of an image acquired from the external apparatus or the recording unit.

In addition, for example, it is assumed that an image shown in FIG. 9 was acquired in the Step 33. The presentation selection unit 15 performed automatic image analysis on this image and as a result acquired words of "mountain forest" and "rain". As a result of search, a similar scene does not exist in the whole images shown in FIG. 9. In this case, the presentation selection unit 15 further searches for a scene similar to "mountain forest" and "rain". The range of search may be the recording unit 5, and an external storage medium may be searched through the Internet line or the like.

In Step 36, the presentation selection unit 15 selects a scene having a relatively high degree of similarity with the image acquired in the Step 33 among the scenes recorded in the recording unit 5 based on the search result in the Step 35. The number of scenes to be selected may be one or more.

In Step 37, the presentation selection unit 15 selects an in-vehicle presentation content including the scene selected in the Step 36 from among the in-vehicle presentation contents recorded in the recording unit 5.

The process proceeds to Step 38 when negative determination is made in the Step 34. In Step 38, the presentation selection unit 15 selects a presentation content having higher associated awakening effect as the wakefulness level estimated in the Step 2 is lower from among the in-vehicle presentation contents recorded in the recording unit 5.

In Step 39, the presentation selection unit 15 determines whether the wakefulness level estimated in the Step 2 is equal to or less than the predetermined threshold value. The process proceeds to Step 40 when the wakefulness level is equal to or less than the threshold value, and proceeds to Step 41 when the wakefulness level exceeds the threshold value.

In Step 40, the presentation selection unit 15 makes the stimulus order in the in-vehicle presentation content selected in any of the Steps 32, 37, and 38 different from the stimulus order recorded in the recording unit 5. The changed stimulus order may be decided at random or may be decided according to some rule.

In Step 41, the presentation selection unit 15 decides the in-vehicle presentation content selected in any of the Steps 32, 37, and 38 as an in-vehicle presentation content used in later-described Step 8. When the processing in the Step 40 is executed, the changed stimulus order is used in Step 8.

Returning to FIG. 5, in Step 8, the presentation execution unit 11 executes in-vehicle presentation on the basis of the in-vehicle presentation content decided in the Step 7. The in-vehicle presentation is provision of the visual stimulus action, auditory stimulus action, tactile stimulus action, and olfactory stimulus action. When one in-vehicle presentation content is decided in the Step 7, the presentation selection unit 15 provides the visual stimulus action, auditory stimulus action, tactile stimulus action, and olfactory stimulus action, according to the visual stimulus information, auditory stimulus information, tactile stimulus information, and olfactory stimulus information included in the one in-vehicle presentation content.

When two or more in-vehicle presentation contents are confirmed in the Step 7, the presentation execution unit 11 combines the visual stimulus information, auditory stimulus information, tactile stimulus information, and olfactory stimulus information included in the two or more in-vehicle presentation contents to provide the visual stimulus action, auditory stimulus action, tactile stimulus action, and olfactory stimulus action. For example, when an in-vehicle presentation content A and an in-vehicle presentation content B are decided in the Step 7, the presentation execution unit 11 can provide, for example, in-vehicle presentation of the in-vehicle presentation content A as the main in-vehicle presentation. However, it is possible to provide it by replacing only the visual stimulus action based on the visual stimulus information included in the in-vehicle presentation content A with the visual stimulus action based on the visual stimulus information included in the in-vehicle presentation content B.

In addition, the presentation execution unit 11 can simultaneously provide a visual stimulus action based on visual stimulus information included in the in-vehicle presentation content A and a visual stimulus action based on visual stimulus information included in the in-vehicle presentation content B. Alternatively, the presentation execution unit 11 can first provide a visual stimulus action based on visual stimulus information included in the in-vehicle presentation content A and then provide a visual stimulus action based on visual stimulus information included in the in-vehicle presentation content B.

In addition, when the image recorded in the external apparatus 39 or the recording unit 5 is a moving image, the presentation execution unit 11 may provide sound recorded in the moving image as an auditory stimulus action. Furthermore, the presentation execution unit 11 may provide change in light similar to change in color of the moving image as a visual stimulus action.

In Step 9, the wakefulness level estimating unit 17 estimates a wakefulness level of a driver as in the Step 2. The wakefulness level estimated in this Step 9 corresponds to a wakefulness level after execution of the in-vehicle presentation.

In Step 10, the effect estimating unit 19 estimates an actual magnitude of awakening effect from the wakefulness level estimated in the Step 2 and the wakefulness level estimated in the Step 9. As an increased amount of the wakefulness level estimated in the Step 9 with respect to the wakefulness level estimated in the Step 2 is larger, the awakening effect is estimated to be higher.

In Step 11, the effect overwriting unit 21 overwrites the value of the actual magnitude of the awakening effect estimated in the Step 10 into a corresponding value of the magnitude of the awakening effect recorded in the recording unit 5.

In Step 12, the driving assistance determination unit 29 acquires the behavior of the own vehicle by using the vehicle behavior sensor 44.

In Step 13, the driving assistance determination unit 29 determines whether the driving assistance is necessary based on the wakefulness level estimated in the Step 9 and the behavior of the own vehicle acquired in the Step 12. As the wakefulness level estimated in the Step 9 is lower, it becomes easier to determine that the driving assistance is necessary. As the behavior of the own vehicle acquired in the Step 12 deviates further from the normal range, it becomes easier to determine that the driving assistance is necessary. The process proceeds to Step 14 when it is determined that the driving assistance is necessary, and proceeds to Step 15 when it is determined that the driving assistance is not necessary.

In Step 14, the driving assistance unit 31 instructs the driving assistance apparatus 53 to execute the driving assistance.

In Step 15, the IG determination unit 33 determines whether an ignition of the own vehicle is on. The process proceeds to Step 1 when the ignition is on, and this processing is terminated when the ignition is off 3. Effects Exerted by the Wakefulness Maintenance Apparatus 1

(1A) The wakefulness maintenance apparatus 1 can execute in-vehicle presentation. Since the in-vehicle presentation includes provision of visual stimulus action, auditory stimulus action, tactile stimulus action, and olfactory stimulus action associated with a scene, a driver can be made to associate the scene with it. Therefore, cognitive activity of the driver increases and memory is recalled, and thereby feeling is changed. That is, a higher-order function of a brain of the driver can be activated. As a result, the driver is harder to be accustomed to the in-vehicle presentation and it is possible to maintain wakefulness of the driver.

(1B) The wakefulness maintenance apparatus 1 acquires an image from the external apparatus 39 or the recording unit 5. Then, the wakefulness maintenance apparatus 1 selects, from the in-vehicle presentation contents, one of the in-vehicle presentation contents, one of the scenes corresponding to the selected one of the in-vehicle presentation contents having a relatively high similarity to the image acquired. The wakefulness maintenance apparatus 1 executes the in-vehicle presentation on the basis of the selected in-vehicle presentation content. Therefore, the driver can be made to associate the scene with it more strongly. As a result, the driver is harder to be accustomed to the in-vehicle presentation and it is possible to further maintain wakefulness of the driver.

(1C) The wakefulness maintenance apparatus 1 preferentially acquires, in the Step 33, an image having a higher preference level of a driver represented by the driver preference information. In addition, an image having a newer date and time when the image was recorded is preferentially acquired. Therefore, the driver can be made to associate the scene with it more strongly and to recall a memory vividly. As a result, the driver is harder to be accustomed to the in-vehicle presentation and it is possible to further maintain wakefulness of the driver.

(1D) The recording unit 5 records in-vehicle presentation contents in association with a corresponding magnitude of awakening effect. The wakefulness maintenance apparatus 1 estimates a first value of a wakefulness level of a driver. The wakefulness maintenance apparatus 1 selects, from the in-vehicle presentation contents recorded in the recording unit 5, one of the presentation contents such that, the lower the first value of the wakefulness level of the driver, the larger the magnitude of awaking effect of the selected one of the presentation contents. Therefore, even when a wakefulness level of a driver is low, it is possible to increase the wakefulness level of the driver by executing an in-vehicle presentation having high awakening effect.

(1E) The wakefulness maintenance apparatus 1 estimates a second value of the wakefulness level after execution of the in-vehicle presentation. The wakefulness maintenance apparatus 1 estimates an actual magnitude of the awakening effect in accordance with the first value of the wakefulness level before execution of the in-vehicle dynamic presentation and the second value of the wakefulness level after execution of the in-vehicle dynamic presentation. The wakefulness maintenance apparatus 1 overwrites an estimated value of the actual magnitude of awakening effect into a corresponding value of the magnitude of the awakening effect recorded in the recording unit 5. Therefore, it is possible to record an accurate magnitude of awakening effect in the recording unit 5.

(1F) A first execution order of the stimulus action is stored in the presentation recording unit, and when the first value of the wakefulness level estimated by the wakefulness level estimating unit is equal to or less than a preset threshold value, the wakefulness maintenance apparatus 1 sets a second execution order of the stimulus action to be different from the first execution order recorded in the recording unit 5. Therefore, an in-vehicle presentation whose unpredictability is high for a driver can be executed. As a result, wakefulness of the driver can be further maintained.

(1G) The wakefulness maintenance apparatus 1 selects, from the in-vehicle presentation contents recorded in the recording unit 5, one of the in-vehicle presentation contents according to the input information received by the input switch 6. Therefore, a driver can select an in-vehicle presentation content according to preference of the driver.

Other Embodiments

The embodiment of the present disclosure is described above, but the present disclosure is not limited to the above-described embodiment and can be variously modified and implemented.

(1) The in-vehicle presentation may be a combination of a plurality of presentation units. Each of the presentation units is a presentation including provision of an auditory stimulus action associated with one scene, and at least one stimulus selected from a group consisting of a visual stimulus action, a tactile stimulus action, and an olfactory stimulus action associated with the one scene. Note that, when the in-vehicle presentation includes one presentation unit, the one presentation unit is an in-vehicle presentation. The in-vehicle presentation in which a plurality of presentation units are combined, for example, can repeatedly create the processing of Step 7 by the number of the presentation units. The plurality of presentation units are provided in a predetermined order.

One of the scenes in presentation unit and another of the scenes in presentation unit may be the same or different from each other. A first scene in the scenes, corresponding to a first unit in the presentation units, and a second scene in the scenes, corresponding to a second unit in the presentation units, are dissimilar to each other, the second unit being immediately next to the first unit. In this case, it is possible to reduce occurrence of habituation of a sensory organ or psychological tiresomeness and to continue recalling memory.

Scenes are dissimilar to each other means that memories recalled by users who see the scenes displayed by a corresponding presentation unit are different from each other. An example in which first and second scenes are dissimilar to each other is a case where information about the first scene is different from the corresponding information about the second scene. The information about each of the first and second scenes can include at least one of the date and time of the corresponding one of the first and second scenes, and the place of the corresponding one of the first and second scenes.

An additional example in which first and second scenes are dissimilar to each other is a case where an average chromatic value and/or an average luminance value of an image corresponding to the first scene displayed in a dramatic representation unit is different from an average chromatic value and/or an average luminance value of an image corresponding to the second scene displayed in the same dramatic representation unit.

A further example in which first and second scenes are dissimilar to each other is a case where (1) The types of one or more stimuli of at least one of the visual stimulus action, auditory stimulus action, tactile stimulus action, olfactory stimulus action, and the like previously set to the first scene are different from the types of one or more stimuli of at least one of the visual stimulus action, auditory stimulus action, tactile stimulus action, olfactory stimulus action, and the like previously set to the second scene, and/or (2) The strengths of one or more stimuli of at least one of the visual stimulus action, auditory stimulus action, tactile stimulus action, olfactory stimulus action, and the like previously set to the first scene are different from the strengths of one or more stimuli of at least one of the visual stimulus action, auditory stimulus action, tactile stimulus action, olfactory stimulus action, and the like previously set to the second scene.

The wakefulness maintenance apparatus 1 can select and combine presentation units in which scenes are dissimilar to each other based on a data and time, a location, a tag, a result of automatic image analysis, and the like to create an in-vehicle presentation.

(2) The in-vehicle presentation may not provide one or two stimuli of the visual stimulus action, tactile stimulus action, and olfactory stimulus action.

(3) When a negative determination is made in the Step 31, the process may always proceed to the Step 38. Alternatively, the process may always proceed to the Step 33 without performing the determination in the Step 31.

(4) The process may always proceed to the Step 41 after the Step 37.

(5) A plurality of functions of one constituent element in the above-described embodiment may be realized by a plurality of constituent elements, or one function of one constituent element may be realized by a plurality of constituent elements. In addition, a plurality of functions of a plurality of constituent elements may be realized by one constituent element, or one function realized by a plurality of constituent elements may be realized by one constituent element. Further, a part of a configuration of the above-described embodiment may be omitted. Furthermore, at least a part of the configuration of the embodiment may be added to or replaced with another configuration of the above-described embodiment. Note that, every aspect included in technical thought specified from wording described in the Claims is an embodiment of the present disclosure.

(6) In addition to the above-described wakefulness maintenance apparatus 1, the present disclosure can be realized by various forms, such as a system using the wakefulness maintenance apparatus 1 as a constituent element, a program causing a computer to function as the control unit 3 of the wakefulness maintenance apparatus 1, a non-transitory tangible recording medium such as a semiconductor memory having recorded the program therein, and a wakefulness maintenance method.

What is claimed is:

1. A wakefulness maintenance apparatus comprising:
a presentation recording unit that records in-vehicle presentation contents each including:
   a corresponding one of scenes,
   an auditory stimulus action associated with the corresponding one of the scenes, and
   at least one stimulus action selected from a group of a visual stimulus action, a tactile stimulus action, and an olfactory stimulus action which are associated with the corresponding one of the scenes; and
a presentation execution unit that executes, based on the in-vehicle presentation contents recorded in the presentation recording unit, an in-vehicle presentation including provision of:
   the auditory stimulus action associated with the corresponding one of the scenes, and
   the at least one stimulus action selected from the group of the visual stimulus action, tactile stimulus action, and olfactory stimulus action which are associated with the corresponding one of the scenes.

2. The wakefulness maintenance apparatus according to claim 1, further comprising:
an image acquiring unit that acquires an image from a recording apparatus capable of recording the image; and
a presentation selection unit that selects, from the in-vehicle presentation contents, one of the in-vehicle presentation contents, one of the scenes corresponding to the selected one of the in-vehicle presentation contents having a relatively high similarity to the image acquired by the image acquiring unit, wherein
the presentation execution unit is configured to execute the in-vehicle presentation based on the selected one of the in-vehicle presentation contents.

3. The wakefulness maintenance apparatus according to claim 2, wherein
the image acquiring unit is configured to preferentially acquire, as the image:
   (A) an image having a newer date and time when the image was recorded, or
   (B) an image for which a driver has a higher preference level.

4. The wakefulness maintenance apparatus according to claim 1, wherein
the presentation recording unit is configured to record each of the in-vehicle presentation contents and a corresponding magnitude of awakening effect of awakening a driver being association with each other,
the wakefulness maintenance apparatus further comprising:
a wakefulness level estimating unit that estimates a first value of a wakefulness level of a driver; and
a presentation selection unit that selects, from the in-vehicle presentation contents recorded in the presentation recording unit, one of the in-vehicle presentation contents such that, the lower the first value of the wakefulness level of the driver, the larger the magnitude of the awakening effect of the selected one of the in-vehicle presentation contents,
the presentation execution unit being configured to execute the in-vehicle presentation on the basis of the selected one of the presentation contents.

5. The wakefulness maintenance apparatus according to claim 4, wherein
the wakefulness level estimating unit is configured to estimate a second value of the wakefulness level after execution of the in-vehicle presentation, and
the wakefulness maintenance apparatus further comprises:
an effect estimating unit that estimates an actual magnitude of the awakening effect in accordance with the first value of the wakefulness level before execution of the in-vehicle presentation and the second value of the wakefulness level after execution of the in-vehicle presentation, and
an effect overwriting unit that overwrites an estimated value of the actual magnitude of the awakening effect into a corresponding value of the magnitude of the awakening effect recorded in the presentation recording unit.

6. The wakefulness maintenance apparatus according to claim 4 wherein
a first execution order of the auditory stimulus action and the at least one stimulus action selected from the group of the visual stimulus action, tactile stimulus action, and olfactory stimulus action is stored in the presentation recording unit, and
when the first value of the wakefulness level estimated by the wakefulness level estimating unit is equal to or less than a preset threshold value, the presentation execution unit is configured to set a second execution order of the auditory stimulus action and the at least one stimulus action selected from the group of the visual stimulus action, tactile stimulus action, and olfactory stimulus action to be different from the first execution order recorded in the presentation recording unit.

7. The wakefulness maintenance apparatus according to claim 1, further comprising:
an input unit that receives information input from an occupant; and
a presentation selection unit selects, from the in-vehicle presentation contents, one of the in-vehicle presentation contents according to the input information received by the input unit, wherein
the presentation execution unit is configured to execute the in-vehicle presentation based on the selected one of the in-vehicle presentation contents.

8. The wakefulness maintenance apparatus according to claim 1, wherein
the in-vehicle presentation comprises a plurality of continuous presentation units each corresponding to one of the scenes, and
a first scene in the scenes, corresponding to a first unit in the continuous presentation units, and a second scene in the scenes, corresponding to a second unit in the continuous presentation units, are dissimilar to each other, the second unit being immediately next to the first unit.

* * * * *